US006284701B1

United States Patent
Yoon et al.

(12) 
(10) Patent No.: US 6,284,701 B1
(45) Date of Patent: *Sep. 4, 2001

(54) METALLOCENE CATALYSTS FOR OLEFIN POLYMERIZATION AND METHOD OF POLYMERIZING OLEFINS USING THE METALLOCENE CATALYSTS

(75) Inventors: Keun-Byoung Yoon; Seok Chang, both of Taejeon; Won-Cheol Jung, Seoul; Yi-Yeol Lyu, Taejeon, all of (KR)

(73) Assignee: Samsung General Chemicals Co., Ltd. (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/294,510

(22) Filed: Apr. 20, 1999

(30) Foreign Application Priority Data

Oct. 13, 1998 (KR) .................................................. 98-42729

(51) Int. Cl.⁷ .............................. B01J 21/00; B01J 21/06; B01J 23/20; B01J 23/24
(52) U.S. Cl. ........................ 502/152; 502/103; 502/104; 502/111; 502/113; 502/117; 502/118; 502/119; 502/120; 502/121; 502/122; 502/123; 502/128; 502/150; 502/155; 502/156; 502/157; 502/167; 502/168; 502/172; 526/943
(58) Field of Search .................................. 502/103, 104, 502/111, 113, 117, 118, 119, 120, 121, 122, 123, 128, 150, 152, 155, 156, 157, 167, 168, 172; 526/943

(56) References Cited

U.S. PATENT DOCUMENTS 3,740,384   6/1973  Ballard et el. ................... 260/94.9 C
6,100,414 *  8/2000  Li et al. ............................... 556/11

FOREIGN PATENT DOCUMENTS 0 423 872 A2   4/1991  (EP) .

* cited by examiner

Primary Examiner—Mark L. Bell
Assistant Examiner—Michael J. DiVerdi
(74) Attorney, Agent, or Firm—Woodcock Washburn Kurtz Mackiewicz & Norris LLP

(57) ABSTRACT

The new metallocene catalysts according to the present invention are prepared by reacting a metallocene compound with a compound having at least two functional groups. The metallocene compound is a transition metal compound, which is coordinated with a main ligand such as cyclopentadienyl group, and an ancillary ligand. The functional groups in the compound are selected from the group consisting of a hydroxyl group, an alkyl or aryl magnesium halide, a thiol group, a primary amine group, a secondary amine group, a primary phosphorous group, a secondary phosphorous group, etc. The metallocene catalysts according to the present invention have a structure in which an ancillary ligand of a metallocene compound is bonded to the functional groups of a compound having at least two functional groups. A structure of the metallocene catalysts can be varied with the type of a metallocene compound and a compound having at least two functional groups, and the molar ratio of each reactant. The metallocene catalysts are employed with a co-catalyst for olefin polymerization. The co-catalyst is an organometallic compound, or a mixture of non-coordinated Lewis acid and alkylaluminium as it is well known in the art.

36 Claims, No Drawings

METALLOCENE CATALYSTS FOR OLEFIN POLYMERIZATION AND METHOD OF POLYMERIZING OLEFINS USING THE METALLOCENE CATALYSTS

FIELD OF THE INVENTION

The present invention relates to new metallocene catalysts for use in preparation of olefin polymers or co-polymers. More specifically, the present invention relates to methods of preparing the metallocene catalysts and methods of preparing olefin polymers such as mono-polymers of ethylene or α-olefin, ethylene/α-olefin co-polymers, propylene/α-olefin co-polymers, etc using the metallocene catalysts.

BACKGROUND OF THE INVENTION

Metallocene catalysts have high activities and are capable of preparing resin with enhanced physical properties in comparison with the resin polymerized by using Ziegler-Natta catalysts. The metallocene catalysts are compounds of Group IV transition metals of the Periodic Table such as titanium, zirconium, hafnium, etc., and have a coordinated structure with a metal compound and ligands composed of one or two groups of cyclopentadienyl, indenyl, fluorenyl or their derivatives. The metallocene catalysts are usually employed with a co-catalyst. And the co-catalyst is normally an alkylaluminoxane such as methylaluminoxane prepared by reacting an alkylaluminium compound with $H_2O$, unlike the co-catalyst employed with the Ziegler-Natta catalysts.

U.S. Pat. No. 3,740,384 discloses a process for polymerization of mono-olefins by contacting the olefin with a catalyst composition containing an organomettallic zirconium complex selected from hydrocarbyl complexes of zirconium in which the valence or co-ordination requirements of the metal are satisfied by alkyl, alkenyl, or arylalkyl groups which may be partially replaced by other monovalent ligands, using the catalyst composition of 1,1,3,3-tetraphenylsiloxane-1,3-diol. The organomettallic zirconium compounds contain allyl, ethylbenzyl, methylene or naphthyl ligands.

EP Publication No. 423 872 A2 discloses a reaction product (for example, $Cp_2ZrR_2$, R=alkyl or halogen) of a silicon of siloxane diol and a dicyclopentadienyl zirconium as a catalyst for ethylene polymerization.

The inventors of the present invention have discovered that the metallocene catalyst prepared by reacting a diol (or diamine, alkyl dimagnesium halide, aryl dimagnesium halide) compound with a cyclopentadienyl zirconium halide has a higher activity in preparation of olefin polymers than conventional catalysts, and that the metallocene catalysts are capable of using less amount of a co-catalyst such as an alkylaluminoxane than conventional catalysts when they are employed in preparation of olefin polymers.

Accordingly, the present inventors have developed new metallocene catalysts for use in preparation of olefin polymers, and methods of preparing the metallocene catalysts and methods of preparing olefin polymers such as mono-polymers of ethylene or α-olefin, ethylene/α-olefin co-polymers, propylene/α-olefin co-polymers, etc using the metallocene catalysts.

OBJECTS OF THE INVENTION

An object of the present invention is to provide metallocene catalysts having a high activity to prepare polyolefins with enhanced physical properties in comparison with the polyolefins prepared by using Ziegler-Natta catalysts.

Another object of the present invention is to provide metallocene catalysts which are capable of using less amount of a co-catalyst such as an alkylaluminoxane than conventional catalysts when they are employed in preparation of olefin polymers.

A further object of the present invention is to provide a method of preparing the metallocene catalysts according to the present invention.

A further object of the present invention is to provide a method of preparing olefin polymers such as mono-polymers of ethylene or α-olefin, ethylene/α-olefin co-polymers, propylene/α-olefin co-polymers, etc using the metallocene catalysts.

Other objects and advantages of this invention will be apparent from the ensuing disclosure and appended claims.

SUMMARY OF THE INVENTION

The new metallocene catalysts according to the present invention are prepared by reacting a metallocene compound with a compound having at least two functional groups. The metallocene compound is a transition metal compound, which is coordinated with a main ligand such as cyclopentadienyl group, and an ancillary ligand. The functional groups in the compound are selected from the group consisting of a hydroxyl group, an alkyl or aryl magnesium halide, a thiol group, a primary amine group, a secondary amine group, a primary phosphorous group, a secondary phosphorous group, etc.

The metallocene catalysts of the present invention can be also prepared by reacting a metallocene compound with the dianion compound produced by reacting an alkali metal compound with a compound having those functional groups.

The metallocene catalysts according to the present invention have a structure in which an ancillary ligand of a metallocene compound is bonded to the functional groups of a compound having at least two functional groups. A structure of the metallocene catalysts can be varied with the type of a metallocene compound and a compound having at least two functional groups, and the molar ratio of each reactant.

The metallocene catalysts are employed with a co-catalyst for olefin polymerization. The co-catalyst is an organomettallic compound, or a mixture of non-coordinated Lewis acid and alkylaluminium as it is well known in the art.

DETAILED DESCRIPTION OF THE INVENTION

The metallocene catalysts according to the present invention are prepared by reacting a metallocene compound with a compound having at least two functional groups. The metallocene catalyst is a transition metal compound, which is coordinated with a main ligand such as cyclopentadienyl group and an ancillary ligand. The functional groups in the compound having at least two functional groups are selected from the group consisting of a hydroxyl group, an alkyl or aryl magnesium halide, a thiol group, a primary amine group, a secondary amine group, a primary phosphorous group, a secondary phosphorous group, etc. The metallocene catalysts of the present invention can be also prepared by reacting a metallocene compound with a dianion compound produced by reacting an alkali metal compound with a compound having those functional groups.

The metallocene catalysts according to the present invention have a structure in which an ancillary ligand of a metallocene compound is bonded to the functional groups of a compound having at least two functional groups. A structure of the metallocene catalysts can be varied with the type of a metallocene compound and a compound having at least two functional groups, and the molar ratio of each reactant.

The metallocene catalysts are employed with a co-catalyst for olefin polymerization. The co-catalyst is an organometallic compound, or a mixture of non-coordinated Lewis acid and alkylaluminium, which is well known in the art. The organometallic compound is usually an alkylaluminoxane, an inorganic compound supported alkylaluminoxane or an organoaluminium compound.

A monomer such as olefin and/or α-olefin is polymerized by using the catalyst system consisting of the metallocene catalysts of the present invention and a co-catalyst. The monomer is mono-polymerized or co-polymerized to prepare olefin polymer or copolymer.

The metallocene catalysts of the present invention are prepared by reacting the metallocene compound represented by the following general formula (A) or (B) with the compound having at least two functional groups represented by the following general formula (C), (D), (E) or (F), and having a structure in which an ancillary ligand of the metallocene compound is bonded to the functional groups of the compound having at least two functional groups:

$(C_nR^1_m)_2MX_2$ or $(C_nR^1_m)R^2(C_nR^1_m)MX_2$      (A)

$(C_nR^1_m)E(R^1_m)J(R^1_m)MX_2$      (B)

wherein M in the formulae (A) and (B) represents a transition metal of Group IV, V or VI of the Periodic Table, preferably of Group IV such as titanium, zirconium, hafnium, etc;

$(C_nR^1_m)$ is a substituted cyclopentadienyl group, a substituted indenyl group or a substituted fluorenyl group, wherein n is an integer of 5, 9, or 13, $R^1$ is a hydrogen atom, an alkyl group of $C_{1-20}$, a cycloalkyl group of $C_{1-20}$, an alkoxy group of $C_{1-20}$, an aryl group of $C_{6-20}$, an alkylaryl group of $C_{6-20}$, an arylalkyl group of $C_{6-20}$, cycloalkyl group of $C_{6-20}$, and m is an integer of 0 to 5;

$R^2$ is an alkyl group of $C_{1-4}$, a silicon, a dialkylgermanium, an alkylphosphine or an alkylamine;

E is O, B, an alkyl group of $C_{1-4}$, a silicon or a dialkylgermanium;

J is S, an alkylphosphine or an alkylamine;

X is a halogen, a hydrogen, an alkyl group of $C_{1-20}$, an alkoxy group of $C_{1-20}$, a branched alkyl group of $C_{1-20}$, a cycloalkyl group of $C_{3-20}$, a substituted cycloalkyl group of $C_{3-20}$; an aryl group of $C_{6-40}$, an alkylaryl group of $C_{6-40}$ or an arylalkyl group of $C_{6-40}$; and $T^2—YR^1Y^1—T^1$      (C)

     (D)

-continued

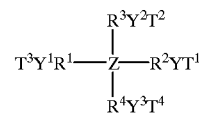
     (E)

$AMgR^5MgA^1$      (F)

wherein $T^1$, $T^2$, $T^3$ and $T^4$ in the formulae (C), (D), (E) and (F) are respectively H, P, S, or an alkali metal such as Na, Li and K;

Y, $Y^1$, $Y^2$ and $Y^3$ are respectively O, S, $—Nr^1$ or $—Pr^2$, wherein $r^1$ and $r^2$ are respectively an hydrogen atom, an alkyl group of $C_{1\sim10}$, a cycloalkyl group of $C_{1\sim10}$, an alkoxy group of $C_{1\sim10}$, an aryl group of $C_{6-20}$, an alkylaryl group of $C_{6-20}$, or an arylalkyl group of $C_{6-20}$;

$R^1$, $R^2$, $R^3$ and $R^4$ respectively represent $R_a$, $R_b—O—R_c$, $—(R_b—O—R_c)$, or

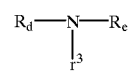

wherein $R_a$, $R_b$, $R_c$, $R_d$ and $R_e$ are respectively a linear alkyl group of $C_{1-20}$, a branched alky group of $C_{1-20}$, a cycloalkyl group of $C_{3\sim20}$, a substituted cycloalkyl group of $C_{3\sim20}$, an aryl group of $C_{6\sim40}$, an alkylaryl group of $C_{6\sim40}$, an arylalkyl group of $C_{6\sim40}$, and $r^3$ is a hydrogen atom, an alkyl group of $C_{1\sim10}$, a cycloalkyl group of $C_{1\sim10}$, an alkoxy group of $C_{1\sim10}$, an aryl group of $C_{6\sim20}$, an alkylaryl group of $C_{6\sim20}$ or an arylalkyl group of $C_{6\sim20}$;

$R^5$ is a linear alkyl group of $C_{1\sim20}$, a branched alkyl group of $C_{1\sim20}$, a substituted cycloalkyl group of $C_{3\sim20}$, or an aryl group of $C_{6\sim20}$, an alkylaryl group of $C_{6\sim20}$ or an arylalkyl group of $C_{6\sim20}$;

Q is N or $—Cr^4$ wherein $r^4$ is an alkyl group of $C_{1\sim10}$, a cycloalkyl group of $C_{1\sim10}$, an alkoxy group of $C_{1\sim10}$, an aryl group of $C_{6\sim20}$, an alkylaryl group of $C_{6\sim20}$ or an arylalkyl group of $C_{6\sim20}$;

Z is C or Si; and

A and $A^1$ are respectively a halogen atom such as F, Cl, Br and I.

The representative examples of the metallocene catalysts according to the present invention are represented by the following general formulae (1)~(11):

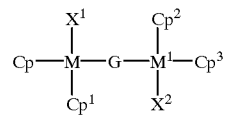
     (1)

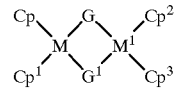
     (2)

(3)

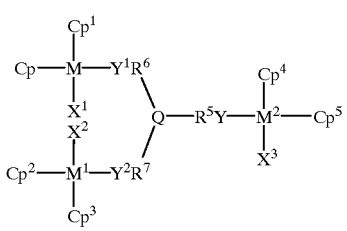

(4)

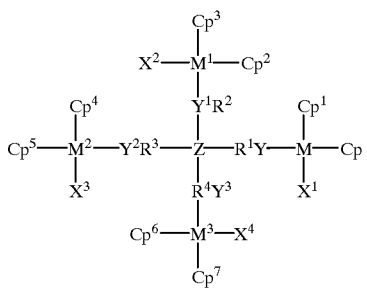

(5)

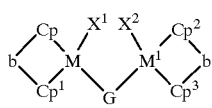

(6)

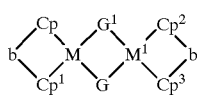

(7)

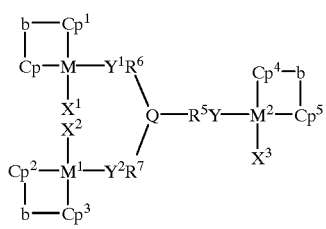

(8)

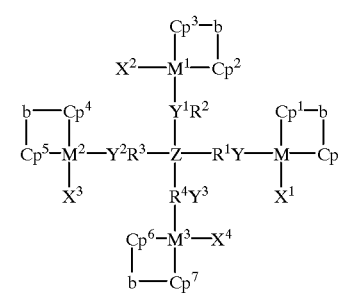

(9)

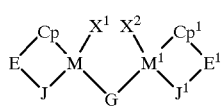

(10)

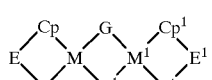

(11)

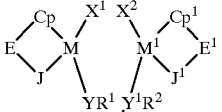

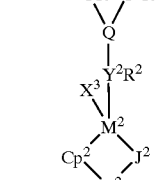

wherein

M, $M^1$, $M^2$ and $M^3$ in the general formulae (1)–(11) are respectively a transition metal of Group IV, V or VI of the Periodic Table, preferably of Group IV such as titanium, zirconium, hafnium, etc;

Cp, $Cp^1$, $Cp^2$, $Cp^3$, $Cp^4$, $Cp^5$, $Cp^6$ and $Cp^7$ are respectively a cyclopentadienyl group, an indenyl group, a fluorenyl group or derivatives thereof, which forms a $\eta^5$-bond with the transition metal of M, $M^1$, $M^2$ or $M^3$;

$X^1$, $X^2$, $X^3$ and $X^4$ are respectively a hydrogen atom, a hydroxyl group, a halogen atom, an alkyl group of $C_{1\sim 20}$, a cycloalkyl group of $C_{1\sim 20}$, an alkoxy group of $C_{1\sim 20}$, an aryl group of $C_{6\sim 20}$, an alkylaryl group of $C_{6\sim 20}$ or an arylalkyl group of $C_{6\sim 20}$;

$R^5$, $R^6$ and $R^7$ are a linear alkyl group of $C_{1\sim 20}$, a branched alkyl group of $C_{1\sim 20}$, a substituted cycloalkyl group of $C_{3\sim 20}$, or an aryl group of $C_{6\sim 20}$, an alkylaryl group of $C_{6\sim 20}$ or an arylalkyl group of $C_{6\sim 20}$;

G, $G^1$ and $G^2$ are respectively a group connecting with two transition metals and represented as —$YR^6Y^1$—, wherein Y and $Y^1$ are respectively O, S, —$Nr^1$ or —$Pr^2$, and $R^6$ is $R_a$, $R_b$—O—$R_c$, —($R_b$—O—$R_c$) or

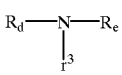

(wherein $R_a$, $R_b$, $R_c$, $R_d$ and $R_e$ are respectively a linear alkyl group of $C_{1-20}$, a branched alkyl group of $C_{1-20}$, a cycloalkyl group of $C_{3-20}$, a substituted cycloalkyl group of $C_{3-20}$, an aryl group of $C_{6-40}$, an alkylaryl group of $C_{6-40}$ or an arylalkyl group of $C_{6-40}$; and $r^1$, $r^2$ and $r^3$ are respectively a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or an arylalkyl group of $C_{6-20}$);

Y, $Y^1$, $Y^2$ and $Y^3$ are respectively O, S, —$Nr^1$ or —$Pr^2$ wherein $r^1$ and $r^2$ are same as defined above;

Z is C, N, Si, Ge or —$Cr^4$ wherein $r^4$ is a linear alkyl group of $C_{1-20}$, a branched alkyl group of $C_{1-20}$, a substituted cycloalkyl group of $C_{3-20}$, an alkoxy group of $C_{3-20}$, an aryl group of $C_{6-20}$, an alkylaryl group of $C_{6-20}$ or an arylalkyl group of $C_{6-20}$);

b is an alkyl group of $C_{1-4}$, a silicon or a dialkylgermanium;

$R^1$ and $R^2$ respectively represent $R_a$, $R_b$—O—$R_c$, —($R_b$—O—$R_c$), or

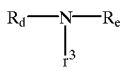

wherein $R_a$, $R_b$, $R_c$, $R_d$ and $R_e$ are respectively a linear alkyl group of $C_{1-20}$, a branched alkyl group of $C_{1-20}$, a cycloalkyl group of $C_{3-20}$, a substituted cycloalkyl group of $C_{3-20}$, an aryl group of $C_{6-40}$, an alkylaryl group of $C_{6-40}$, an arylalkyl group of $C_{6-40}$, and $r^3$ is a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or an arylalkyl group of $C_{6-20}$;

Q is N or —$Cr^{19}$ (wherein $r^{19}$ is an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or arylalkyl group of $C_{6-20}$);

E, $E^1$, and $E^2$ are O, B, an alkyl group of $C_{1-4}$, Si or dialkylgermanium; and J, $J^1$ and $J^2$ are respectively S, alkylphosphine or alkylamine.

The metallocene catalyst of formula (1) is prepared by reacting $(C_nR^1_m)_2MX_2$ (A) and the compound of formulae (C) or (F) with an equivalent ratio of 2:1.

The metallocene catalyst of formula (2) is prepared by reacting $(C_nR^1_m)_2MX_2$ (A) and the compound of formulae (C) or (F) with an equivalent ratio of 1:1.

The metallocene catalyst of formula (3) is prepared by reacting $(C_nR^1_m)_2MX_2$ (A) and the compound of formula (D) with an equivalent ratio of 3:1.

The metallocene catalyst of formula (4) is prepared by reacting $(C_nR^1_m)_2MX_2$ (A) and the compound of formula (E) with an equivalent ratio of 4:1.

The metallocene catalyst of formula (5) is prepared by reacting $(C_nR^1_m)R^2(C_nR^1_m)MX_2$ (A) and the compound of formulae (C) or (F) with an equivalent ratio of 2:1.

The metallocene catalyst of formula (6) is prepared by reacting $(C_nR^1_m)R^2(C_nR^1_m)MX_2$ (A) and the compound of formulae (C) or (F) with an equivalent ratio of 1:1.

The metallocene catalyst of formula (7) is prepared by reacting $(C_nR^1_m)R^2(C_nR^1R_m)MX_2$ (A) and the compound of formula (D) with an equivalent ratio of 3:1.

The metallocene catalyst of formula (8) is prepared by reacting $(C_nR^1_m)R^2(C_nR^1_m)MX_2$ (A) and the compound of formula (E) with an equivalent ratio of 2:1.

The metallocene catalyst of formula (9) is prepared by reacting $(C_nR^1_m)E(R^1_m)J(R^1_m)MX_2$ (B) and the compound of formulae (C) or (F) with an equivalent ratio of 2:1.

The metallocene catalyst of formula (10) is prepared by reacting $(C_nR^1_m)E(R^1_m)J(R^1_m)MX_2$ (B) and the compound of formulae (C) or (F) with an equivalent ratio of 1:1.

The metallocene catalyst of formula (11) is prepared by reacting $(C_nR^1_m)E(R^1_m)J(R^1_m)MX_2$ (B) and the compound of formula (D) with an equivalent ratio of 3:1.

A metallocene compound used for preparing the metallocene catalyst according to the present invention is commercially available. Also, the metallocene compound may be prepared according to a method which is conventionally well known. The metallocene compound can be prepared by a method comprising the steps of preparing a salt-state ligand compound containing alkali metal by reacting a cyclopentadienyl ligand derivative with an alkali metal or an alkali metal compound, introducing a siliconz or tin compound to the salt-state ligand compound, and reacting the above resultant compound with a Group IV transition metal compound. In case of substituting an ancillary ligand of a metallocene compound to an alkoxy group, an alkyl group or any other groups, the metallocene compound is reacted with the desired equivalent of an alcohol or an alkali metal compound. The above-described method for preparing the metallocene compound may be easily performed by an ordinary skilled person in the art to which this technology pertains. Examples of the alkali metals are K. Na and thallium, and those of the alkali metal compounds are n-butyllithium, sec-butyllithium, tert-butyllithium, methyllithium, sodium methoxide, sodium ethoxide, etc. The Group IV transition metal compounds of the Periodic Table include titanium tetrachloride, zirconium tetrachloride and hafnium tetrachloride, etc.

The representative examples of the metallocene compound which can used in this invention include:
bis(cyclopentadienyl)zirconium dichloride,
bis(cyclopentadienyl)zirconium methylchloride,
bis(cyclopentadienyl)zirconium dimethyl,
bis(methylcyclopentadienyl)zirconium dichloride,
bis(methylcyclopentadienyl)zirconium methylchloride,
bis(methylcyclopentadienyl)zirconium dimethyl,
bis(ethylcyclopentadienyl)zirconium dichloride,
bis(ethylcyclopentadienyl)zirconium methylchloride,
bis(ethylcyclopentadienyl)zirconium dimethyl,
bis(pentamethylcyclopentadienyl)zirconium dichloride,
bis(pentamethylcyclopentadienyl)zirconium methyichloride,
bis(pentamethylcyclopentadienyl)zirconium dimethyl,
bis(n-butyl-cyclopentadienyl)zirconium dichloride,
bis(n-butyl-cyclopentadienyl)zirconium methylchloride,
bis(n-butyl-cyclopentadienyl)zirconium dimethyl,
bis(indenyl)zirconium dichloride,
bis(indenyl)zirconium methylchloride,
bis(indenyl)zirconium dimethyl,
bid(2-methyl-indenyl)zirconium dichloride,
bis(2-methyl-indenyl)zirconium methylchloride,
bis(2-methyl-indenyl)zirconium dimethyl,
bis(2-phenyl-indenyl)zirconium dichloride,
bis(2-phenyl-indenyl)zirconium methylchloride,
bis(2-phenyl-indenyl)zirconium dimethyl,
dimethylsilylbis(cyclopentadienyl)zirconium dichloride,
dimethylsilylbis(cyclopentadienyl)zirconium methylchloride,
dimethylsilylbis(cyclopentadienyl)zirconium dimethyl,
dimethylsilylbis(indenyl)zirconium dichloride,
dimethylsilylbis(indenyl)zirconium methylchloride,
dimethylsilylbis(indenyl)zirconium dimethyl,
dimethylsilylbis(2-methyl-indenyl)zirconium dichloride,
dimethylsilylbis(2-methyl-indenyl)zirconium methylchloride,
dimethylsilylbis(2-methyl-indenyl)zirconium dimethyl,
dimethylsilyl(indenylcyclopentadienyl)zirconium dichloride,
dimethylsilyl(indenylcyclopentadienyl)zirconium methylchloride,
dimethylsilyl(indenylcyclopentadienyl)zirconium dimethyl,
dimethylsilyl(fluorenylcyclopentadienyl)zirconium dichloride,
dimethylsilyl(fluorenylcyclopentadienyl)zirconium methylchloride,
dimethylsilyl(fluorenylcyclopentadienyl)zirconium dimethyl,
ethylenebis(cyclopentadienyl)zirconium dichloride,
ethylenebis(cyclopentadienyl)zirconium methylchloride,
ethylenebis(cyclopentadienyl)zirconium dirnethyl,
ethylenebis(indenyl)zirconium dichloride,
ethylenebis(indenyl)zirconium methylchloride, ethylenebis(indenyl)zirconium dimethyl,
ethylenebis(2-methyl-indenyl)zirconium dichloride,
ethylenebis(2-methyl-indenyl)zirconium methylchloride,
ethylenebis(2-methyl-indenyl)zirconium dimethyl,
ethylene(indenylcyclopentadienyl)zirconium dichloride,
ethylene(indenylcyclopentadienyl)zirconium methylchloride,
ethylene(indenylcyclopentadienyl)zirconium dimethyl,
ethylene(fluorenylcyclopentadienyl)zirconium dichloride,
ethylene(fluorenylcyclopentadienyl)zirconium methylchloride,
ethylene(fluorenylcyclopentadienyl)zirconium dimethyl,
isopropylbis(cyclopentadienyl)zirconium dichloride,
isopropylbis(cyclopentadienyl)zirconium methylchloride,
isopropylbis(cyclopentadienyl)zirconium dimethyl,
isopropylbis(indenyl)zirconium dichloride,
isopropylbis(indenyl)zirconium methylchloride,
isopropylbis(indenyl)zirconium dimethyl,
isopropylbis(2-methyl-indenyl)zirconium dichloride,
isopropylbis(2-methyl-indenyl)zirconium methylchloride,
isopropylbis(2-methyl-indenyl)zirconium dimethyl,
isopropyl(indenylcyclopentadienyl)zirconium dichloride,
isopropyl(indenylcyclopentadienyl)zirconium methylchloride,
isopropyl(indenylcyclopentadienyl)zirconium dimethyl,
isopropyl(fluorenylcyclopentadienyl)zirconium dichloride,
isopropyl(fluorenylcyclopentadienyl)zirconium methylchloride, and
isopropyl(fluorenylcyclopentadienyl)zirconium dimethyl.

The representative examples of the compound having at least two functional groups, which reacts with the metallocene compound in this invention, include:
1,3-bis(diphenylphosphino)propane ethyleneglycol, 1,3-propanediol, 1,2-propanediol,
(s)-(+)-1,2-propanediol,
2-methyl-1,3-propanediol, 2,2-dimethyl-1,3-propanediol,
2-ethyl-2-methyl-1,3-propanediol, 2,2-diethyl-1,3-propanediol,
2-methyl-2-propyl-1,3-propanediol, 2-butyl-2-ethyl-1,3-propanediol,
1,4-butanediol, (±)-1,3-butanediol, (R)-(−)-1,3-butanediol, (S)-(+)-1,3-butanediol, (±)-1,2-butanediol, 2,3-butanediol, meso-2,3-butanediol, (2R,3R)-(−)-2,3-butanediol,
(2S,3S)-(+)-2,3-butanediol, 3,3-dimethyl-1,2-butanediol, pinacol,
1,5-pentanediol, 1,4-pentanediol, 1,2-pentanediol, 2,4-pentanediol,
(2R,4R)-(−)-pentanediol, (2S,4S)-(+)-pentanediol,
2-methyl-2,4-pentanediol, (R)-(−)-2-methyl-2,4-pentanediol,
2,4-dimethyl-2,4-pentanediol, 2,2,4-trimethyl-1,3-pentanediol,
1,6-hexanediol, 1,5-hexanediol, (±)-1,2-hexanediol, 2,5-hexanediol,
2-ethyl-1,3-hexanediol, 2,5-dimethyl-2,5-hexanediol, 1,7-heptanediol,
1,8-octanediol, 1,2-octanediol, 1,9-nonanediol, 1,10-decanediol,
1,2-decanediol, 1,12-dodecanediol, (±)-1,2-dodecanediol,
cis-1,2-cyclopentanediol, trans-1,2-cyclopentanediol, 1,3-cyclopentanediol,
trans-1,2-cyclohexanediol, 1,2-cyclohexanediol, 1,4-cyclohexanediol,
2,5-dimethylcyclohexane-1,4-diol, 2,5-isopropylcyclohexane-1,4-diol,
cis-1,2-cyclohexanedimethanol, 1,4-cyclohexanedimethanol,
(+)-cis-p-menthane-3,8-diol, (−)-trans-p-menthane-3,8-diol,
(±)-trans-1,2-cycloheptanediol, cis-1,2-cyclooctanediol,
trans-1,2-cyclooctanediol, 1,4-cyclooctanediol, cis-1,5-cyclooctanediol,
4,8-bis(hydroxymethyl)tricyclo[5.2.1.0$^{2,6}$]-decane,
(1R,2R,3S,5R)-(−)-pinanediol, 1,5-decalindiol,
3-cyclohexane-1,1-dimethanol, (±)-trans-2-cyclohexane-1,4-diol,
trans-p-ment-6-ene-2,8-diol, cis-3,5-cyclohexadiene-1,2-diol
5-norbonene-2,2-dimethanol,
(±)-(2-endo,3-exo)-bicyclo[2.2.2]-oct-5-ene-2,3-dimethanol, glycerol,
1,1,1-tris(hydorxymethyl)ethane, (R)-(+)-1,2,4-butanetriol,
(S)-(−)-1,2,4-butanetriol, 2-ethyl-2-(hydroxymethyl)-1,3-propanediol,
(±)-1,2,3-trihydroxyhexane, 1,2,6-trihydroxyhexane, ethanolamine,
2-hydroxyethylhydrazine, 3-amino-1-propanol,
DL-1-amino-2-propanol,
4-amino-1-butanol, (±)-2-amino-1-butanol, 5-amino-1-pentanol,
DL-2-amino-1-pentanol, 6-amino-1-hexanol,
2-(2-aminoethoxy)ethanol,
2-(methylamino)ethanol, 2-(ethylamino)ethanol,
2-(propylamino)ethanol,
diethanolamine, diisopropanolamine, 2-(butylamino) ethanethiol,
N-methyldiethanolamine, N-ethyldiethanolamine,
N-butyldiethanolamine,
triethanolamine, triisopropanolamine,
1-[N,N-bis(2-hydroxyethyl)amino]-2-propanol, catechol,
3-methylcatechol, 4-methylcatechol, 4-tert-butylcatechol,
DL-3,4-dihydroxyphenylglycol, 3,5-diisopropylcatechol,
3,5-di-tert-butylcatechol, resorcinol, 2-methylresorcinol,
4-ethylresorcinol,
4-hexylresorcinol, 4-dodecylresorcinol, 5-pentylresorcinol,
5-pentadecylresorcinol, 2,5-dimethylresorcinol,
hydroquinone, methylhydroquinone, tert-butylhydroquinone,
2,3-dimethylhydroquinone, 2,5-di-tert-butylhydroquinone,
2,5-bis(1,1,3,3-tetramethylbutyl)hydroquinone, trimethylhydroquinone,
1,2-dihydroxynaphthalene, 1,3-dihydroxynaphthalene,
1,4-dihydroxynaphthalene, 1,5-dihydroxynaphthalene,
1,6-dihydroxynaphthalene, 2,3-dihydroxynaphthalene,
2,6-dihydroxynaphthalene, 2,7-dihydroxynaphthalene,
bis(2-hydroxyphenyl)methane, (±)-hydrobenzoin, meso-hydrobenzoin,
(R,R)-(+)-hydrobenzoin, (S,S)-(−)-hydrobenzoin, benzopinacole,
1,4-benzenedimethanol,
α, α, α', α'-tetramethyl-1,4-benzenedimethanol,
1,5-dihydroxy-1,2,3,4-tetrahydronaphthalene, 2,2'-biphenyldimethanol,
3-(3,5-di-tert-butyl-4-hydroxyphenyl)-1-propanol,
(±)-1-phenyl-1,2-ethanediol, (S)-(+)-1-phenyl-1,2-ethanediol,
(R)-(−)-1-phenyl-1,2-ethanediol,
(R)-(+)-1,1,2-triphenyl-1,2-ethanediol,
2,2'-biphenol, 4,4'-biphenol, phenylhydroquinone,
bis(4-hydroxyphenyl)methane, 4,4'-isopropylidenediphenol,
2,2-bis(4-hydroxy-3-methylphenyl)propane,
1,1,1-tri(4-hydroxyphenyl)ethane, meso-hexestrol, 1,2-ethanedithiol,
1,3-propanedithiol, 1,2-propanedithiol, 1,4-butanedithiol, 1,3-butanedithiol,
1,5-pentanedithiol, 1,6-hexanedithiol, 1,8-octanedithiol, 1,9-nonanedithiol,
2-mercaptoethanol, 1-mercapto-2-propanol, 3-mercapto-2-butanol,
3-mercapto-1,2-propanediol, 2,3-dimercapto-1-propanol, dithiothreitol,
dithioerythreitol, 2-mercaptoethylether, 1,4-dithiane-2,5-diol,
2,5-dimethyl-2,5-dihydroxy-1,4-dithiane,
1,5,9,13-tetrathiacyclohexadecane-3,11-diol,
1,5,9,13,17,21-hexathiacyclotetracosane-3,11,19-triol, ethylenediamine,
1,3-diaminopropane, 1,2-diaminopropane, 1,4-diaminobutane,
1,2-diamino-2-methylpropane, 1,6-hexanediamine, 1,7-diaminoheptane,
1,8-diaminooctane, 2,5-dimethyl-2,5-hexanediamine, 1,9-diaminononane,
1,10-diaminodecane, 1,12-diaminododecane, spermidine,
4,4'-methylenebis(cyclohexylamine),
4,4'-methylenebis(2-methylcyclohexylamine), 1,4-diaminocyclohexane,
1,3-cyclohexanebis(methylamine), 1,8-diamino-p-methane,
4,4'-trimethylenedipiperidine, 2-piperidinethanol, 3-piperidinethanol,
4-hydroxypiperidine, 4,4'-trimethylenebis(1-piperidinethanol),
2,2,6,6-tetramethyl-4-piperidinol, piperazine, 2,6-dimethylpiperazine,
1,4-bis(2-hydroxyethyl)piperazine, homopiperazine,
1,4,7-triazacyclononane, 1,5,9-triazacyclododecane, cyclene,
1,4,8,11-tetraazacyclotetradecane, 1,4,8,12-tetraazacyclotetradecane,
2-anilinoethanol, N-phenyldiethanolamine, 3-aminophenol,
3-aminothiophenol, 4,4'-ethylenedianiline, 3,3'-methylenedianiline,
4,4'-methylenedianiline, 4-aminophenyl ether, 4-aminophenol,
4-aminophenethyl alcohol, 4,4'-methylenebis(2,6-dimethylaniline),
4,4'-methylenebis(2,6-diethylaniline),
4,4'-methylenebis(2,6-diisopropylaniline), 3,3',5,5'-tetramethylbenzidine,
1,4-phenylenediamine, N,N'-diphenyl-1,4-phenylenediamine,
2,7-diaminofluorene, N,N'-dibenzylethylenediamine, (±)-syneprine and
4-hydroxy-4-phenylpiperidine.

The dihalogenalkyl compound used in Grinard reaction is dibromoethane, dibromopropane, dibromobutane, dibromopentane, dibromohexane, dibromoheptane, dibromooctane, dibromodecane, dibromododecane, dibromohexadecane, dibromooctadecane, dichloroethane, dichloropropane, dichlorobutane, dichloropentane, dichlorohexane, dichloroheptane, dichlorooctane, dichlorodecane, dichlorohexadecane, or dichlorooctadecane.

In case of preparing the metallocene catalysts by reacting a metallocene compound with the compound having at least two functional groups in an organic solvent, the molar ratio of a transition metal in the metallocene compound to the functional groups of the compound having at least two functional groups is in the range from 1:1 to 1:10, the reaction temperature being in the range from −100° C. to 150° C., and the reaction time being in the range from 0.1 to 120 hours.

The metallocene catalysts according to the present invention are employed with a co-catalyst in order to prepare a polyolefin. The co-catalyst is an organometallic compound or a mixture of a non-coordinated Lewis acid and an alkylaluminium. Examples of the organometallic compound are an alkylaluminoxane and an organoaluminium compound. Examples of the alkylaluminoxane are a methylaluminoxane (MAO) and a modified methylaluminoxane (MMAO).

The organoaluminium compound is an aluminoxane having the structural unit represented by the general formula (16). There are two types of aluminoxanes. One is an aluminoxane having a chain structure represented by the general formula (17), the other is an aluminoxane having a cyclic structure represented by the general formula (18):

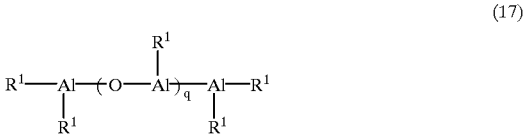

wherein $R^1$ is an alkyl group of $C_{1-8}$ and q is an integer of 2 to 100.

The component ratio of the new metallocene catalyst to the co-catalyst is determined with the molar ratio of a transition metal of Group IV in the metallocene catalyst to the aluminium in the organometallic compound. Preferably, the molar ratio of the transition metal to aluminium is in the range from 1:1 to 1:20000 and more preferably in the range from 1:5 to 1:3000.

Examples of the non-coordinated Lewis acid used as co-catalyst in the present invention include N,N'-dimethylanilinium tetrakis(pentafluorophenyl)borate, triphenylcarbeniumtetrakis(pentafluorophenyl)borate, ferroceriumtetrakis(pentafluorophenyl)borate and tris(pentafluorophenyl)borate.

Examples of the alkylaluminium compound used as co-catalyst in the present invention include ethylaluminium, triethylaluminium, diethylaluminium chloride, ethylaluminium dichloride, triisobutylaluminium, diisobutylaluminium hydride, diisobutylaluminium chloride, tri(n-butyl)aluminium, tri(n-hexyl)aluminium, tri(n-octyl)aluminium and ethylaluminium sesquichloride.

The molar ratio of the non-coordinated Lewis acid to a transition metal in the catalyst system according to the present invention is preferably in the range from 0.1:1 to 20:1. The molar ratio of the alkylaluminum to a transition metal in the catalyst system is preferably in the range from 1:1 to 1000:1.

The reaction temperature for olefin polymerization using the catalyst system according to the present invention is preferably in the range from 0 to 200° C. and the reaction time is preferably in the range from 30 to 240 minutes.

Unsaturated olefin monomers are polymerized with the catalyst system according to the present invention. In one embodiment of the process of polymerization, the co-catalyst is added to a polymerization reactor first, the metallocene catalyst prepared in accordance with the present invention is added to the reactor, and olefin monomers are added to the reactor, consecutively. In another embodiment of this invention, both the metallocene compound and the compound having at least two functional groups may be reacted in a polymerization reactor to prepare a metallocene catalyst, and then the co-catalyst and monomers may be added to the polymerization reactor, consecutively.

Copolymers can be prepared using the metallocene catalyst according to the present invention. For copolymerization, at least two monomers are selected from the group consisting of an unsaturated α-olefin, a cycloolefin, a diene, a vinylketone, an acrolein, an acrylonitrile, an acrylamide, a vinylacetate and a styrene. This copolymerization may be carried out by adding a co-catalyst, a co-monomer, a metallocene catalyst and a monomer to the polymerization reactor, consecutively. Alternatively, the coploymerization may be carried out by reacting the metallocene compound and the compound having at least two functional groups in a polymerization reactor to prepare a metallocene catalyst, and adding a co-catalyst and monomers to the polymerization reactor.

The unsaturated α-olefin being contacted with the catalyst system according to the present invention is represented by the general formula (19):

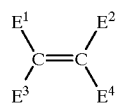
(19)

wherein $E^1$, $E^2$, $E^3$ and $E^4$ are respectively a hydrogen atom; a halogen atom; and a group containing at least one atom selected from the group consisting of C, O, Si, P, S, Se and Sn.

The illustrative examples of the olefin monomer represented by the formula (19) are α-olefin, cyclic olefin, diene, vinylketone, acrolein, acrylonitrile, acrylamide, acrylic acid, and vinylacetate.

Examples of α-olefin include ethylene, propylene, 1-butene, 1-hexene, 1-octene, 1-decene, 1-dodecene, 1-hexadecene and 1-octadecene.

Examples of cyclic olefin include cyclobutene, cyclopentene, cyclohexene, 3-methylcyclopentene, 3-methylcyclohexene, norbonene, phenylnorbonene and dimethylnorbonene.

Examples of diene include 1,3-butadiene, isoprene, 1-ethoxy-1,3-butadiene, chloroprene, 4-methyl-1,3-pentadiene, 7-methyl-1,6-octadiene, 1,5-hexadiene, 1,7-octadiene, and 1,9-decadiene.

Examples of vinylketone include methylvinylketone, phenylvinylketone, ethylvinylketone, and n-propylvinylketone.

Examples of acrolein include acrolein and metacrolein.

Examples of acrylonitrile include vinylidenecyanide, methoxyacrylonitrile, and phenylacrylonitrile.

Examples of acrylamide include N-methylacrylamide, N-ethylacryl amide, and N-isopropylacrylamide.

Examples of acrylic acid include aryl acrylate, isopropyl acrylate, ethyl acrylate, acrylic acid chloride, and undecenoic acid.

Examples of vinylacetate include vinylacetate and vinylthioacetate.

The present invention may be better understood by reference to the following examples which are intended for purposes of illustration and are not to be confined as in any way limiting the scope of the present invention, which is defined in the claims appended hereto.

EXAMPLES 1~18: SYNTHESIS OF CATALYST

Example 1

Catalyst 1

Toluene of 150 ml was added to a round-bottomed flask containing 0.1 mmol (0.29 g) of $Cp_2ZrCl_2$ (biscyclopentadienyl zirconium dichloride), and the solution was put into a reactor. The temperature of the reactor was kept at −78° C. Bisphenol-A of 0.05 mmol (0.23 g) was added to a second flask, toluene of 50 ml was added, and 0.2 mmol (0.2 ml) of triethylamine was added with syringe to the second flask. The solution of the second flask was slowly added to the reactor. After adding, the temperature of the reactor was slowly increased up to room temperature. After reaction in the reactor for 12 hours, the resulting solution was filtered to obtain a light yellowish solution. The light yellowish solution was evaporated under vacuum to remove toluene. Bimetallic compound (catalyst 1) bridged with bisphenol-A was obtained as yield of 85%.

Example 2

Catalyst 2

Toluene of 50 ml was added to a round-bottomed flask containing 0.1 mmol (0.29 g) of $Cp_2Cl_2$., and the solution was put into a reactor. The temperature of the reactor was kept at −78° C. Bisphenol-A dianion of 0.05 mmol (0.23 g) was added to a second flask, toluene of 50 ml was added, and 0.2 mmol (0.2 ml) of triethylamine was added with syringe to the second flask. The solution of the second flask was slowly added to the reactor. After adding, the temperature of the reactor was slowly increased up to room temperature. After reaction in the reactor for 12 hours, the resulting solution was filtered to obtain a light yellowish solution. The light yellowish solution was evaporated under vacuum to remove toluene. Bimetallic compound (catalyst 2) bridged with bisphenol-A was obtained as yield of 75%.

Example 3

Catalyst 3

Catalyst 3 was prepared in the same method as in Example 1 except that $Cp^*_2ZrCl_2$ (bispentamethylcyclopentadienyl zirconium dichloride) was used instead of $Cp_2ZrCl_2$.

Example 4

Catalyst 4

Catalyst 4 was prepared in the same method as in Example 1 except that $(n-BuCp)_2ZrCl_2$ (bis(n-butylcyclopentadienyl) zirconium dichloride) was used instead of $Cp_2ZrCl_2$.

Example 5

Catalyst 5

Catalyst 5 was prepared in the same method as in Example 1 except that 0.1 mmol (0.46 g) of bisphenol-A and 0.4 mmol (0.4 ml) of triethylamine were used. Catalyst 5 has two bridges connected with bisphenol-A.

Example 6

Catalyst 6

Catalyst 6 was prepared in the same method as in Example 5 except that $(n-BuCp)_2ZrCl_2$ was used instead of $Cp_2ZrCl_2$.

Example 7
Catalyst 7

Catalyst 7 was prepared in the same method as in Example 1 except that 0.05 mmol of hydroquinone was used instead of bisphenol-A. Catalyst 7 was bridged with hydroquinone.

Example 8
Catalyst 8

Catalyst 8 was prepared in the same method as in Example 7 except that 0.1 mmol of hydroquinone was used. Catalyst 8 has two bridges connected with hydroquinone.

Example 9
Catalyst 9

Catalyst 9 was prepared in the same method as in Example 7 except that $(n-BuCp)_2ZrCl_2$ was used instead of $Cp_2ZrCl_2$.

Example 10
Catalyst 10

Catalyst 10 was prepared in the same method as in Example 8 except that $(n-BuCp)_2ZrCl_2$ was used instead of $Cp_2ZrCl_2$.

Example 11
Catalyst 11

Catalyst 11 was prepared in the same method as in Example 1 except that $Et(Ind)_2ZrCl_2$ (ethylenebisindenyl zirconium dichloride) was used instead of $Cp_2ZrCl_2$.

Example 12
Catalyst 12

Catalyst 12 was prepared in the same method as in Example 1 except that $Me_2Si(Ind)_2ZrCl_2$ (dimethylsilylbisindenyl zirconium dichloride) was used instead of $Cp_2ZrCl_2$.

Example 13
Catalyst 13

Catalyst 13 was prepared in the same method as in Example 1 except that $Me_4CpSiMe_2N(t-Bu)TiCl_2$ (tert-butylamidodimethyltetramethylcyclopentadienyl)silane titanium dichloride) was used instead of $Cp_2ZrCl_2$.

Example 14
Catalyst 14

Catalyst 14 was prepared in the same method as in Example 1 except that $Me_2SiCp_2ZrCl_2$ (dimethylsilylbiscyclopentadienyl zirconium dichloride) instead of $Cp_2ZrCl_2$.

Example 15
Catalyst 15

Catalyst 15 was prepared in the same method as in Example 5 except that $Me_2SiCp_2ZrCl_2$ was used instead of $Cp_2ZrCl_2$.

Example 16
Catalyst 16

Ether of 50 ml was added to a round-bottomed flask containing 0.1 mmol (0.29 g) of $Cp_2ZrCl_2$ (biscyclopentadienyl zirconium dichloride), and the solution was put into a reactor. The temperature of the reactor was kept at −78° C. $BrMg(CH_2)_{10}MgBr$ of 0.1 mmol (0.23 g) was added to a second flask, and ether of 50 ml was added to the second flask. The solution of the second flask was slowly added to the reactor. After adding, the temperature of the reactor was slowly increased up to room temperature. After reaction in the reactor for 12 hours, the resulting solution was filtered. The filtered solution was evaporated under vacuum to remove ether. Bimetallic compound (catalyst 16) bridged with an alkyl was obtained.

Example 17
Catalyst 17

Catalyst 17 was prepared in the same method as in Example 7 except that $Cp_2HfCl_2$ (biscyclopentadienyl halfnium dichloride) was used instead of $Cp_2ZrCl_2$.

Example 18
Catalyst 18

Toluene of 50 ml was added to a round-bottomed flask containing 0.3 mmol of $(n-BuCP)_2ZrCl_2$ (bis(n-butylcyclopentadienyl) zirconium dichloride), and the solution was put into a reactor. The temperature of the reactor was kept at −78° C. Triol (α, α, α-tris(4-hydroxyphenyl)-1-ethyl-4-isopropylbenzene) of 0.1 mmol was added to a second flask, toluene of 50 ml was added, and 0.4 mmol (0.4 ml) of triethylamine was added with syringe to the second flask. The solution of the second flask was slowly added to the reactor. After adding, the temperature of the reactor was slowly increased up to room temperature. After reaction in the reactor for 12 hours, the resulting solution was filtered to obtain a white solution. The white solution was evaporated under vacuum to remove toluene. Bimetallic compound (catalyst 18) bridged with a triol was obtained as yield of 88%.

Example 19
Ethylene Polymerization

Ethylene polymerization was performed by using the new metallocene catalysts prepared in the Examples. The results are shown in Table 1.

TABLE 1

| Catalyst | [Al]/[M] | Temperature (° C.) | Reaction time (hr) | Yield (g) | Activity (kg-PE/mol-M) |
|---|---|---|---|---|---|
| Catalyst 4 | 25 | 80 | 1 | 32 | 16.0 |
| Catalyst 4 | 50 | 80 | 1 | 64 | 32.0 |
| Catalyst 4 | 75 | 80 | 1 | 74 | 37.0 |
| Catalyst 9 | 25 | 80 | 1 | 49 | 24.5 |
| Catalyst 9 | 50 | 80 | 1 | 73 | 36.5 |
| Catalyst 16 | 50 | 80 | 1 | 28 | 14.0 |
| Catalyst 16 | 75 | 80 | 1 | 32 | 16.0 |
| Catalyst 18 | 75 | 80 | 1 | 20 | 10.0 |
| Catalyst 18 | 50 | 80 | 1 | 51 | 25.5 |
| Catalyst 18 | 75 | 80 | 1 | 65 | 32.5 |

*polymerization condition: hexane(1L), ethylene(115 psi)

Example 20
Ethylene/1-hexene Co-polymerization

Copolymerization of ethylene and 1-hexene was performed by using the new metallocene catalysts in the Examples. The results are shown in Table 2.

TABLE 2

| Catalyst | [Al]/[M] | Temperature (° C.) | Reaction time (hr) | Yield (g) | Activity (kg-PE/mol-M) |
|---|---|---|---|---|---|
| Catalyst 4 | 50 | 80 | 1 | 72 | 36.0 |
| Catalyst 4 | 75 | 80 | 1 | 89 | 44.5 |

*polymerization condition: hexane(1L), 1-hexene(25mL) and ethylene(115 psi)

The present invention can be easily carried out by an ordinary skilled person in the art. Many modifications and changes may be deemed to be within the scope of the present invention as defined in the following claims.

What is claimed is:

1. A metallocene catalyst for olefin polymerization, which is prepared by reacting:

a metallocene compound represented by the general formulae (A) or (B); and a compound having at least two functional groups represented by the general formulae (C), (D), or (E):

$(C_nR^1_m)_2MX_2$ or $(C_nR^1_m)R^2(C_nR^1_m)MX_2$     (A)

$(C_nR^1_m)E(R^1_m)J(R^1_m)MX_2$     (B)

$T^2—YR^1Y^1—T^1$     (C)

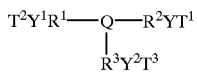     (D)

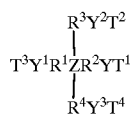     (E)

wherein M in the formulae (A) and (B) is a transition metal of Group IV, V or VI of the Periodic Table;

$(C_nR^1_m)$ is a substituted cyclopentadienyl group, a substituted indenyl group or a substituted fluorenyl group, wherein n is an integer of 5, 9, or 13, $R^1$ in formula (A) and (B) is a hydrogen atom, an alkyl group of $C_{1-20}$, a cycloalkyl group of $C_{1-20}$, an alkoxy group of $C_{1-20}$, an aryl group of $C_{6-20}$, an alkylaryl group of $C_{6-20}$, an arylalkyl group of $C_{6-20}$, cycloalkyl group of $C_{6-20}$, and m is an integer of 0 to 5;

$R^2$ in formula (A) is an alkyl group of $C_{1-4}$, a silicon, a dialkylgermanium, an alkylphosphine, or an alkylamine;

E is O, B, an alkyl group of $C_{1-4}$, a silicon, or a dialkylgermanium;

J is S, an alkylphosphine, or an alkylamine;

X is a halogen, a hydrogen, an alkyl group of $C_{1-20}$, an alkoxy group of $C_{1-20}$, a branched alkyl group of $C_{1-20}$, a cycloalkyl group of $C_{3-20}$, a substituted cycloalkyl group of $C_{3-20}$, an aryl group of $C_{6-40}$, an alkylaryl group of $C_{6-40}$, or an arylalkyl group of $C_{6-40}$;

$T^1$, $T^2$, $T^3$ and $T^4$ in the formulae (C), (D), and (E) are H, P, S, or an alkali metal;

Y, $Y^1$, $Y^2$ and $Y^3$ are O, S, —$Nr^1$, or —$Pr^2$, wherein $r^1$ and $r^2$ are a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$, or an arylalkyl group of $C_{6-20}$;

$R^1$, $R^2$, $R^3$ and $R^4$ in formulas (C), (D), and (E) are $R_a$, $R_b$—O—$R_c$, —($R_b$—O—$R_c$), or

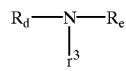

wherein $R_a$, $R_b$, $R_c$, $R_d$ and $R_e$ are a linear alkyl group of $C_{1-20}$, a branched alkyl group of $C_{1-20}$, a cycloalkyl group of $C_{3-20}$, a substituted cycloalkyl group of $C_{3-20}$, an aryl group of $C_{6-40}$, an alkylaryl group of $C_{6-40}$, an arylalkyl group of $C_{6-40}$, and $r^3$ is a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or an arylalkyl group of $C_{6-20}$;

Q is N or —$Cr^4$ wherein $r^4$ is an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or an arylalkyl group of $C_{6-20}$; and Z is C, Si or Ge.

2. The metallocene catalyst for olefin polymerization of claim 1 wherein said metallocene compound is selected from the group consisting of bis(cyclopentadienyl)zirconium dichloride, bis(ethylcyclopentadienyl)zirconium dichloride, bis(pentamethylcyclopentadienyl)zirconium dichloride, bis(n-butyl-cyclopentadienyl)zirconium dichloride, bis(indenyl)zirconium dichloride, bis(2-methylindenyl)zirconium dichloride, dimethylsilylbis(cyclopentadienyl)zirconium dichloride, dimethylsilylbis(indenyl)zirconium dichloride, dimethylsilylbis(2-methylindenyl)zirconium dichloride, ethylenebis(cyclopentadienyl)zirconium dichloride, ethylenebis(indenyl)zirconium dichloride, ethylenebis(2-methylindenyl)zirconium dichloride, isopropylbis(indenyl)zirconium dichloride, and isopropyl(fluorenylcyclopentadienyl)zirconium dichloride.

3. The metallocene catalyst for olefin polymerization of claim 1 wherein said compound having at least two functional groups is selected from the group consisting of 1,6-hexanediol, 1,8-octanediol, 1-[N,N-bis(2-hydroxyethyl)amino]-2-propanol, hydroquinone, 1,5-dihydroxynaphthalene, 4,4'-isopropylidenediphenol, 2,2-bis(4-hydroxy-3-methylphenyl)propane, 1,6-hexanedithiol, 1,6-hexanediamine, spermidine, 4,4'-methylenebis(cyclohexylamine), 4-hydroxypiperidine, 4,4'-methylenebis(2,6-diethylaniline), 4,4'-methylenebis(2,6-diisopropylaniline), and 1,3-bis(diphenylphosphino)propane.

4. The metallocene catalyst for olefin polymerization of claim 1, which is represented by the general formula (2):

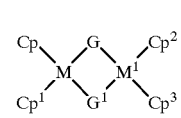     (2)

wherein M and $M^1$ are a transition metal of Group IV, V or VI of the Periodic Table;

Cp, $Cp^1$, $Cp^2$ and $Cp^3$ are a cyclopentadienyl group, an indenyl group, a fluorenyl group, or derivatives thereof, which forms a $\eta^5$-bond with the transition metal of M and $M^1$;

G and $G^1$ are the same or different and are each represented as —$YR^6Y^1$, wherein Y and $Y^1$ are O, S, —$Nr^1$ or —$Pr^2$, and $R^6$ is $R_a$, $R_b$—O—$R_c$, —($R_b$—O—$R_c$) or

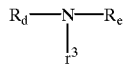

wherein $R_a$, $R_b$, $R_c$, $R_d$ and $R_e$ are a linear alkyl group of $C_{1-20}$, a branched alkyl group of $C_{1-20}$, a cycloalkyl group of $C_{3-20}$, a substituted cycloalkyl group of $C_{3-20}$, an aryl group of $C_{6-40}$, an alkylaryl group of $C_{6-40}$ or an arylalkyl group of $C_{6-40}$; and $r^1$, $r^2$ and $r^3$ are a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or an arylalkyl group of $C_{6-20}$.

5. The metallocene catalyst for olefin polymerization of claim 1, which is represented by the general formula (3):

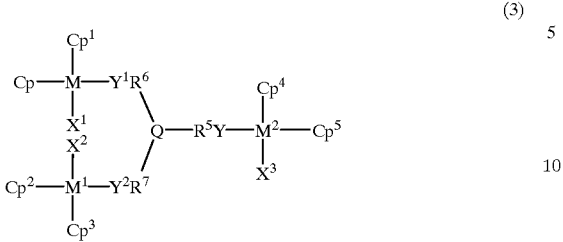

(3)

wherein M, M¹ and M² are a transition metal of Group IV, V or VI of the Periodic Table;

Cp, Cp¹, Cp², Cp³, Cp⁴, and Cp⁵ are the same or different and are each a cyclopentadienyl group, an indenyl group, a fluorenyl group or derivatives thereof, which forms a $\eta^5$-bond with the transition metal of M, M¹, or M²;

$X^1$, $X^2$ and $X^3$ are a hydrogen atom, a hydroxyl group, a halogen atom, an alkyl group of $C_{1-20}$, a cycloalkyl group of $C_{1-20}$, an alkoxy group of $C_{1-20}$, an aryl group of $C_{6-20}$, an alkylaryl group of $C_{6-20}$, or an arylalkyl group of $C_{6-20}$;

Y, $Y^1$ and $Y^2$ are O, S, —$Nr^1$ or —$Pr^2$, wherein $r^1$ and $r^2$ are a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$, or an arylalkyl group of $C_{6-20}$;

Q is N or —$Cr^{19}$, wherein $r^{19}$ is an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or arylalkyl group of $C_{6-20}$; and $R^5$, $R^6$ and $R^7$ are a linear alkyl group of $C_{1-20}$, a branched alkyl group of $C_{1-20}$, a substituted cycloalkyl group of $C_{3-20}$, an aryl group of $C_{6-20}$, an alkylaryl group of $C_{6-20}$ or an arylalkyl group of $C_{6-20}$.

6. The catalyst for olefin polymerization of claim 1, which is represented by the general formula (4):

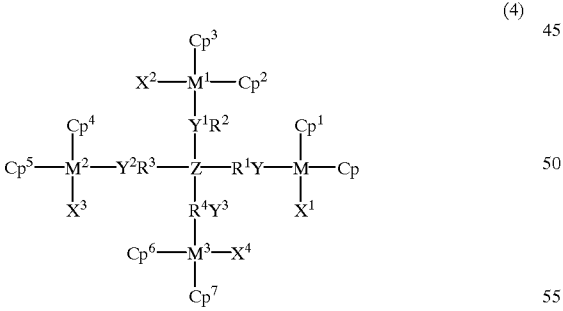

(4)

wherein M, M¹, M², and M³ transition metals of Group IV, V or VI of the Periodic Table;

Cp, Cp¹, Cp², Cp³, Cp⁴, Cp⁵, Cp⁶ and Cp⁷ are the same or different and are each a cyclopentadienyl group, an indenyl group, a fluorenyl group, or derivatives thereof, which forms a $\eta^5$-bond with the transition metal of M, M¹, M² or M³;

$X^1$, $X^2$, $X^3$, and $X^4$ are a hydrogen atom, a hydroxyl group, a halogen atom, an alkyl group of $C_{1-20}$, a cycloalkyl group of $C_{1-20}$, an alkoxy group of $C_{1-20}$, an aryl group of $C_{6-20}$, an alkylaryl group of $C_{6-20}$, or an arylalkyl group of $C_{6-20}$;

Y, $Y^1$, $Y^2$, and $Y^3$ are O, S, —$Nr^1$ or —$Pr^2$, wherein $r^1$ and $r^2$ are a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$, or an arylalkyl group of $C_{6-20}$;

$R^1$, $R^2$, $R^3$, and $R^4$ are $R_a$, $R_b$—O—$R_c$, —($R_b$—O—$R_c$), or

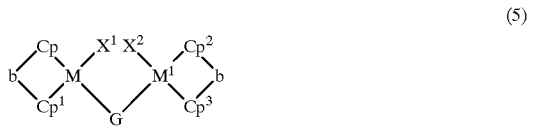

wherein $R_a$, $R_b$, $R_c$, $R_d$ and $R_e$ are a linear alkyl group of $C_{1-20}$, a branched alkyl group of $C_{1-20}$, a cycloalkyl group of $C_{3-20}$, a substituted cycloalkyl group of $C_{3-20}$, an aryl group of $C_{6-40}$, an alkylaryl group of $C_{6-40}$, an arylalkyl group of $C_{6-40}$, and $r^3$ is a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or an arylalkyl group of $C_{6-20}$; and Z is C or Si.

7. The metallocene catalyst for olefin poymerization of claim 1, which is represented by the general formula (5):

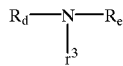

(5)

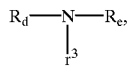

wherein M and M¹ are a transition metal of Group IV, V or VI of the Periodic Table;

Cp, Cp¹, Cp², and Cp³ are the same or different and are each a cyclopentadienyl group, an indenyl group, a fluorenyl group, or derivatives thereof, which forms a $\eta^5$-bond with the transition metal of M or M¹;

$X^1$ and $X^2$ are a hydrogen atom, a hydroxyl group, a halogen atom, an alkyl group of $C_{1-20}$, a cycloalkyl group of $C_{1-20}$, an alkoxy group of $C_{1-20}$, an aryl group of $C_{6-20}$, an alkylaryl group of $C_{6-20}$, or an arylalkyl group of $C_{6-20}$;

G is a group represented as —$YR^6Y^1$, wherein Y and $Y^1$ are O, S, —$Nr^1$ or —$Pr^2$; and $R^6$ is $R_a$, $R_b$—O—$R_c$, —($R_b$—O—$R_c$) or wherein $R_a$, $R_b$, $R_c$, $R_d$ and $R_e$ are a linear alkyl group of $C_{1-20}$, a branched alkyl group of $C_{1-20}$, a cycloalkyl group of $C_{3-20}$, a substituted cycloalkyl group of $C_{3-20}$, an aryl group of $C_{6-40}$, an alkylaryl group of $C_{6-40}$ or an arylalkyl group of $C_{6-40}$; and $r^1$, $r^2$ and $r^3$ are a hydrogen atom, an alkyl group of $C_{1-10}$, a cycloalkyl group of $C_{1-10}$, an alkoxy group of $C_{1-10}$, an aryl group of $C_{6-20}$, an alkylaryl group of $C_{6-20}$ or an arylalkyl group of $C_{6-20}$; and b is an alkyl group of $C_{1-4}$, Si, dialkylgermanium, alkylphosphine or alkylamine.

8. The metallocene catalyst for olefin polymerization of claim 1, which is represented by the general formula (6):

(6)

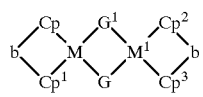

wherein M and M$^1$ are a transition metal of Group IV, V or VI of the Periodic Table;

Cp, Cp$^1$, Cp$^2$, and Cp$^3$ are a cyclopentadienyl group, an indenyl group, a fluorenyl group, or derivatives thereof, which forms a η$^5$-bond with the transition metal of M or M$^1$;

G and G$^1$ are the same or different and are each a group represented as —YR$^6$Y$^1$, wherein Y and Y$^1$ are O, S, —Nr$^1$ or —Pr$^2$; and R$^6$ is R$_a$, R$_b$—O—R$_c$, —(R$_b$—O—R$_c$) or

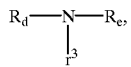

wherein R$_a$, R$_b$, R$_c$, R$_d$ and R$_e$ are a linear alkyl group of C$_{1-20}$, a branched alkyl group of C$_{1-20}$, a cycloalkyl group of C$_{3-20}$, a substituted cycloalkyl group of C$_{3-20}$, an aryl group of C$_{6-40}$, an alkylaryl group of C$_{6-40}$ or an arylalkyl group of C$_{6-40}$; and r$^1$, r$^2$ and r$^3$ are a hydrogen atom, an alkyl group of C$_{1-10}$, a cycloalkyl group of C$_{1-10}$, an alkoxy group of C$_{1-10}$, an aryl group of C$_{6-20}$, an alklaryl group of C$_{6-20}$ or an arylalkyl group of C$_{6-20}$; and b is an alkyl group of C$_{1-4}$, Si, dialkylgermanium, alkylphosphine or alkylamine.

9. The metallocene catalyst for olefin polymerization of claim 1, which is represented by the general formula (7):

(7)

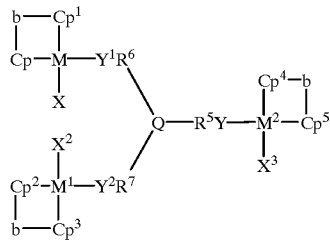

wherein M, M$^1$ and M$^2$ are a transition metal of Group IV, V or VI of the Periodic Table;

Cp, Cp$^1$, Cp$^2$, Cp$^3$, Cp$^4$, and Cp$^5$ are the same or different and are each a cyclopentadienyl group, an indenyl group, a fluorenyl group, or derivatives thereof, which forms a η$^5$-bond with the transition metal of M, M$^1$, or M$^2$;

X$^1$, X$^2$ and X$^3$ are a hydrogen atom, a hydroxyl group, a halogen atom, an alkyl group of C$_{1-20}$, a cycloalkyl group of C$_{1-20}$, an alkoxy group of C$_{1-20}$, an aryl group of C$_{6-20}$, an alkylaryl group of C$_{6-20}$, or an arylalkyl group of C$_{6-20}$;

Y, Y$^1$ and Y$^2$ are O, S, —Nr$^1$ or —Pr$^2$, wherein r$^1$ and r$^2$ are a hydrogen atom, an alkyl group of C$_{1-10}$, a cycloalkyl group of C$_{1-10}$, an alkoxy group of C$_{1-10}$, an aryl group of C$_{6-20}$, an alkylaryl group of C$_{6-20}$, or an arylalkyl group of C$_{6-20}$;

Q is N or —Cr$^{19}$, wherein r$^{19}$ is an alkyl group of C$_{1-10}$, a cycloalkyl group of C$_{1-10}$, an alkoxy group of C$_{1-10}$, an aryl group of C$_{6-20}$, an alkylaryl group of C$_{1-20}$ or arylalkyl group of C$_{6-20}$;

R$^5$, R$^6$ and R$^7$ are a linear alkyl group of C$_{1-20}$, a branched alkyl group of C$_{1-20}$, a substituted cycloalkyl group of C$_{3-20}$, an aryl group of C$_{6-20}$, an alkylaryl group of C$_{6-20}$ or an arylalkyl group of C$_{6-20}$; and b is an alkyl group of C$_{1-4}$, Si, dialkylgermanium, alkylphosphine or alkylamine.

10. The metallocene catalyst for olefin polymerization of claim 1, which is represented by the general formula (8):

(8)

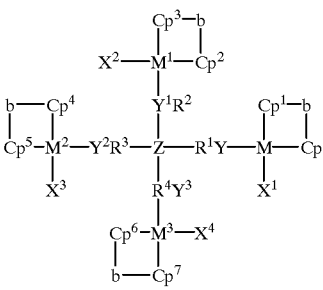

wherein M, M$^1$, M$^2$, and M$^3$ are a transition metal of Group IV, V or VI of the Periodic Table;

Cp, Cp$^1$, Cp$^2$, Cp$^3$, Cp$^4$, Cp$^5$, Cp$^6$, and Cp$^7$ are the same or different and are each a cyclopentadienyl group, an indenyl group, a fluorenyl group or derivatives thereof, which forms a η$^5$-bond with the transition metal of M, M$^1$, M$^2$ or M$^3$;

X$^1$, X$^2$, X$^3$ and X$^4$ are a hydrogen atom, a hydroxyl group, a halogen atom, an alkyl group of C$_{1-20}$, a cycloalkyl group of C$_{1-20}$, an alkoxy group of C$_{1-20}$, an aryl group of C$_{6-20}$, an alkylaryl group of C$_{6-20}$, or an arylalkyl group of C$_{6-20}$;

Y, Y$^1$, Y$^2$ and Y$^3$ are O, S, —Nr$^1$ or —Pr$^2$, wherein r$^1$ and r$^2$ are a hydrogen atom, an alkyl group of C$_{1-10}$, a cycloalkyl group of C$_{1-10}$, an alkoxy group of C$_{1-10}$, an aryl group of C$_{6-20}$, an alkylaryl group of C$_{6-20}$, or an arylalkyl group of C$_{6-20}$;

R$^1$, R$^2$, R$^3$, and R$^4$ in formula (8) are R$_a$, R$_b$—O—R$_c$, —(R$_b$—O—R$_c$), or

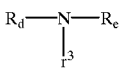

wherein R$_a$, R$_b$, R$_c$, R$_d$ and R$_e$ are a linear alkyl group of C$_{1-20}$, a branched alkyl group of C$_{1-20}$, a cycloalkyl group of C$_{3-20}$, a substituted cycloalkyl group of C$_{3-20}$, an aryl group of C$_{6-40}$, an alkylaryl group of C$_{6-40}$, an arylalkyl group of C$_{6-40}$, and r$^3$ is a hydrogen atom, an alkyl group of C$_{1-10}$, a cycloalkyl group of C$_{1-10}$, an alkoxy group of C$_{1-10}$, an aryl group of C$_{6-20}$, an alkylaryl group of C$_{6-20}$ or an arylalkyl group of C$_{6-20}$;

Z is C or Si; and b is an alkyl group of C$_{1-4}$, Si, dialkylgermanium, alkylphosphine or alkylamine.

11. The metallocene catalyst for olefin polymerization of claim 1, which is represented by the general formula (9):

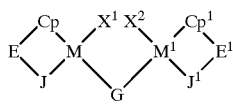

(9)

wherein M and M$^1$ are a transition metal of Group IV, V or VI of the Periodic Table;

Cp and Cp$^1$ are a cyclopentadienyl group, an indenyl group, a fluorenyl group, or derivatives thereof, which forms a η$^5$-bond with the transition metal of M and M$^1$;

X$^1$ and X$^2$ are a hydrogen atom, a hydroxyl group, a halogen atom, an alkyl group of C$_{1-20}$, a cycloalkyl group of C$_{1-20}$, an alkoxy group of C$_{1-20}$, an aryl group of C$_{6-20}$, an alkylaryl group of C$_{6-20}$, or an arylalkyl group of C$_{6-20}$;

G is a group connecting with two transition metals and represented as —YR$^6$Y$^1$, wherein Y and Y$^1$ are O, S, —Nr$^1$ or —Pr$^2$, and R$^6$ is R$_a$, R$_b$—O—R$_c$, —(R$_b$—O—R$_c$) or

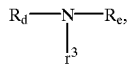

wherein R$_a$, R$_b$, R$_c$, R$_d$ and R$_e$ are a linear alkyl group of C$_{1-20}$, a branched alkyl group of C$_{1-20}$, a cycloalkyl group of C$_{3-20}$, a substituted cycloalkyl group of C$_{3-20}$, an aryl group of C$_{6-40}$, an alkylaryl group of C$_{6-40}$ or an arylalkyl group of C$_{6-40}$; and r$^1$, r$^2$ and r$^3$ are a hydrogen atom, an alkyl group of C$_{1-10}$, a cycloalkyl group of C$_{1-10}$, an alkoxy group of C$_{1-10}$, an aryl group of C$_{6-20}$, an alkylaryl group of C$_{6-20}$ or an arylalkyl group of C$_{6-20}$;

E and E$^1$ are O, B, an alkyl group of C$_{1-4}$, Si or dialkylgermanium; and

J and J$^1$ are S, alkylphosphine or alkylamine.

12. The metallocene catalyst for olefin polymerization of claim 1, which is represented by the general formula (10):

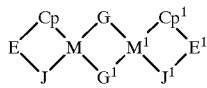

(10)

wherein M and M$^1$ are a transition metal of Group IV, V or VI of the Periodic Table;

Cp and Cp$^1$ are a cyclopentadienyl group, an indenyl group, a fluorenyl group, or derivatives thereof, which forms a η$^5$-bond with the transition metal of M and M$^1$;

G and G$^1$ are the same or different and are each a group connecting with two transition metals and represented as —YR$^6$Y$^1$, wherein Y and Y$^1$ are O, S, —Nr$^1$ or —Pr$^2$, and R$^6$ is R$_a$, R$_b$—O—R$_c$, —(R$_b$—O—R$_c$) or

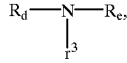

wherein R$_a$, R$_b$, R$_c$, R$_d$ and R$_e$ are a linear alkyl group of C$_{1-20}$, a branched alkyl group of C$_{1-20}$, a cycloalkyl group of C$_{3-20}$, a substituted cycloalkyl group of C$_{3-20}$, an aryl group of C$_{6-40}$, an alkylaryl group of C$_{6-40}$ or an arylalkyl group of C$_{6-40}$; and r$^1$, r$^2$ and r$^3$ are a hydrogen atom, an alkyl group of C$_{1-10}$, a cycloalkyl group of C$_{1-10}$, an alkoxy group of C$_{1-10}$, an aryl group of C$_{6-20}$, an alkylaryl group of C$_{6-20}$, or an arylalkyl group of C$_{6-20}$;

E and E$^1$ are O, B, an alkyl group of C$_{1-4}$, Si or dialkylgermanium; and

J and J$^1$ are S, alkylphosphine or alkylamine.

13. The metallocene catalyst for olefin polymerization of claim 1, which is represented by the general formula (11):

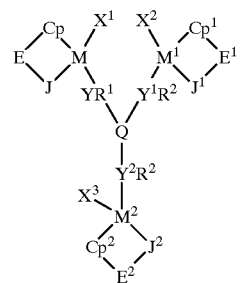

(11)

wherein M, M$^1$ and M$^2$ are a transition metal of Group IV, V or VI of the Periodic Table;

Cp, Cp$^1$ and Cp$^2$ are a cyclopentadienyl group, an indenyl group, a fluorenyl group, or derivatives thereof, which forms a η$^5$-bond with the transition metal of M, M$^1$, or M$^2$;

X$^1$, X$^2$ and X$^3$ are a hydrogen atom, a hydroxyl group, a halogen atom, an alkyl group of C$_{1-20}$, a cycloalkyl group of C$_{1-20}$, an alkoxy group of C$_{1-20}$, an aryl group of C$_{6-20}$, an alkylaryl group of C$_{6-20}$, or an arylalkyl group of C$_{6-20}$;

Y, Y$^1$ and Y$^2$ are O, S, —Nr$^1$ or —Pr$^2$ wherein r$^1$ and r$^2$ are a hydrogen atom, an alkyl group of C$_{1-10}$, a cycloalkyl group of C$_{1-10}$, an alkoxy group of C$_{1-10}$, an aryl group of C$_{6-20}$, an alkylaryl group of C$_{6-2}$, or an arylalkyl group of C$_{6-20}$;

R$^1$ and R$^2$ in formula (11) are R$_a$, R$_b$—O—R$_c$, —(R$_b$—O—R$_c$), or

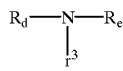

wherein R$_a$, R$_b$, R$_c$, R$_d$ and R$_e$ are a linear alkyl group of C$_{1-20}$, a branched alkyl group of C$_{1-20}$, a cycloalkyl group of C$_{3-20}$, a substituted cycloalkyl group of C$_{3-20}$, an aryl group of C$_{6-40}$, an alkylaryl group of C$_{6-40}$, an arylalkyl group of C$_{6-40}$, and r$^3$ is a hydrogen atom, an alkyl group of C$_{1-10}$, a cycloalkyl group of C$_{1-10}$, an alkoxy group of C$_{1-10}$, an aryl group of C$_{6-20}$, an alkylaryl group of C$_{6-20}$, or an arylalkyl group of C$_{6-20}$;

Q is N or —Cr$^{19}$, wherein r$^{19}$ is an alkyl group of C$_{1-10}$, a cycloalkyl group of C$_{1-10}$, an alkoxy group of C$_{1-10}$, an aryl group of C$_{6-20}$, an alkylaryl group of C$_{6-20}$ or arylalkyl group of C$_{6-20}$;

E, E$^1$ and E$^2$ are O, B, an alkyl group of C$_{1-4}$, Si or dialkylgermanium; and J, J$^1$ and J$^2$ are S, alkylphosphine or alkylamine.

14. The metallocene catalyst for olefin polymerization of claim 1 wherein the molar ratio of the transition metal of said metallocene compound to the functional group of said compound having at least two functional groups is in the range from about 1:1 to about 1:10.

15. A catalyst system for olefin polymerization comprising the metallocene catalyst according to claim 1 and a co-catalyst.

16. The catalyst system of claim 15 wherein said co-catalyst is an organometallic compound.

17. The catalyst system of claim 16 wherein said organometallic compound is selected from the group consisting of alkylaluminoxane, organoaluminium compound, and a mixture thereof.

18. The catalyst system of claim 17 wherein said aluminoxane is selected from the group consisting of methylaluminoxane, modified methylaluminoxane, silica-supported aluminoxane, magnesium compound-supported aluminoxane, alumina-supported aluminoxane and polymer-supported aluminoxane.

19. The catalyst system of claim 18 wherein said aluminoxane has a chain structure and a cyclic structure respectively represented by the general formulae (H) or (I), having a structural unit represented by the general formula (G):

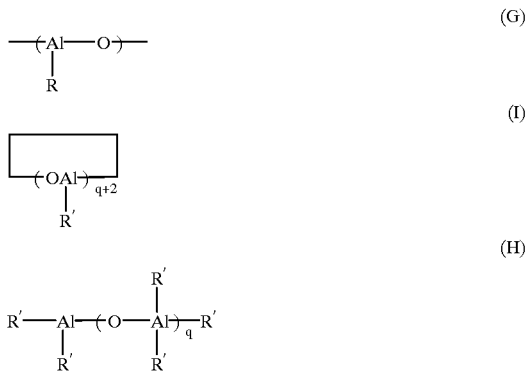

wherein $R^1$ is an alkyl group of $C_{1-8}$ and q is an integer of 2 to 100.

20. The catalyst system of claim 17 wherein the molar ratio of transition metal of said metallocene compound to aluminium of said organometallic compound is in the range from about 1:1 to about 1:20000.

21. The catalyst system of claim 20 wherein said molar ratio is in the range from about 1:5 to about 1:3000.

22. The catalyst system of claim 15 wherein said co-catalyst is a mixture of a non-coordinated Lewis acid and alkylaluminium.

23. The catalyst system of claim 22 wherein said non-coordinated Lewis acid is selected from the group consisting of N,N-dimethylaniliniumtetrakis(pentafluoro-phenyl)borate, triphenylcarbeniumtetrakis(pentafluorophenyl)borate, ferrocerium tetrakis(pentafluorophenyl)borate and tris(pentafluorophenyl)borate.

24. The catalyst system of claim 22 wherein the molar ratio of transition metal of said catalyst to said non-coordinated Lewis acid is in the range from about 1:0.1 to about 1:20.

25. The catalyst system of claim 22 wherein said alkylaluminium is selected from the group consisting of ethylaluminium, triethylaluminium, diethylaluminium chloride, ethylaluminium dichloride, triisobutylaluminium, diisobutylaluminium hydride, diisobutylaluminium chloride, tri(n-butyl)aluminium, tri(n-hexyl)aluminium, tri(n-octyl)aluminium and ethylaluminium sesquichloride.

26. The catalyst system of claim 25 wherein the molar ratio of said transition metal of said catalyst to said alkylaluminium is in the range from about 1:1 to about 1:1000.

27. The catalyst system of claim 26 wherein said molar ratio is in the range from about 1:50 to about 1:500.

28. A method of olefin polymerization comprising contacting an unsaturated olefin with the catalyst system according to claim 15.

29. The method of claim 28 comprising the consecutive steps of adding the co-catalyst to a polymerization reactor, adding the metallocene catalyst to the reactor, and adding the olefin monomers to the reactor.

30. The method of claim 28 comprising the consecutive steps of reacting the metallocene compound and the compound having at least two functional groups in a polymerization reactor to prepare a metallocene catalyst, and adding the co-catalyst and monomers to the polymerization reactor.

31. The method of claim 28 wherein said contacting step is performed at a temperature of about 0–200° C. for about 30–240 minutes.

32. A method of co-polymerization comprising contacting at least two monomers selected from the group consisting of unsaturated α-olefin, cycloolefin, diene, vinylketone, acrolein, acrylonitrile, acrylamide, vinylacetate and styrene with the catalyst system of claim 15.

33. The method of claim 32 comprising the consecutive steps of adding the co-catalyst, one of said monomers, the metallocene catalyst, and the other monomer to the polymerization reactor.

34. The method of claim 32 comprising the consecutive steps of reacting the metallocene compound and the compound having at least two functional groups in a polymerization reactor to prepare a metallocene catalyst, and adding the co-catalyst and monomers to the polymerization reactor.

35. The method of claim 32 wherein said contacting step is performed at the temperature of about 0–200° C. for about 30–240 minutes.

36. The metalocene catalyst for olefin polymerization of claim 1 wherein M in the formulae (A) and (B) is a transition metal of Group IV of the Periodic Table.

* * * * *